US00PP12418P2

(12) United States Plant Patent
Zaiger et al.

(10) Patent No.: US PP12,418 P2
(45) Date of Patent: Feb. 26, 2002

(54) NECTARINE TREE NAMED: 'HONEY FIRE'

(76) Inventors: Chris Floyd Zaiger, 929 Grimes Ave.; Gary Neil Zaiger, 1907 Elm Ave.; Leith Marie Gardner, 1207 Grimes Ave.; Grant Gene Zaiger, 4005 California Ave., all of Modesto, CA (US) 95358

( * ) Notice: Subject to any disclaimer, the term of this patent is extended or adjusted under 35 U.S.C. 154(b) by 8 days.

(21) Appl. No.: 09/841,543

(22) Filed: Apr. 24, 2001

(51) Int. Cl.[7] ..... A01H 5/00
(52) U.S. Cl. ..... Plt./190
(58) Field of Search ..... Plt./190

*Primary Examiner*—Bruce R. Campell
*Assistant Examiner*—Anne Marie Grünberg

(57) ABSTRACT

A new and distinct variety of nectarine tree (*Prunus persica* var. *nucipersica*). The features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices such as, pruning, thinning, spraying, irrigation, and fertilization. Its novelty consist of the following unique combination of desirable features that are outstanding in a new variety:

1. Heavy and regular production of fruit.
2. Fruit with a sweet, mild, sub-acid flavor.
3. Fruit with a high degree of attractive red skin color.
4. Relatively uniform size fruit throughout the tree.
5. Fruit holding firm on the tree 7 to 8 days after maturity (shipping ripe).
6. A tree with a relatively low winter chilling requirement of approximately 400 to 450 hours below 45° F.
7. Fruit ripening in the early maturity season.

1 Drawing Sheet

BACKGROUND OF THE VARIETY

In the field of plant genetics, we conduct an extensive and continuing plant-breeding program including the organization and asexual reproduction of orchard trees, and of which plums, peaches, nectarines, apricots, cherries and interspecifics are exemplary. It was against this background of our activities that the present variety of nectarine tree was originated and asexually reproduced by us in our experimental orchard located near Modesto, Stanislaus County, Calif.

PRIOR VARIETIES

Among the existing varieties of nectarines and peaches which are known to us, and mentioned herein, 'Royal Glo' Nectarine (U.S. Plant Pat. No. 8,281), 'Honey Kist' Nectarine (U.S. Plant Pat. No. 9,333) and 'Golden Supreme' Peach (non-patented).

ORIGIN OF THE VARIETY

The new and distinct variety of nectarine tree, (*Prunus persica* var. *nucipersica*), was developed by us in our experimental orchard located near Modesto, Calif. as a first generation cross between two seedlings with field identification numbers 111LB51 and 204LF555. The maternal parent (111LB51) originated from a cross of a nectarine seedling of unknown parentage with 'Golden Supreme' Peach (non-patented). The paternal parent (204LF555) originated from a cross between 'Honey Kist' Nectarine (U.S. Plant Pat. No. 9,333) and 'Royal Glo' Nectarine (U.S. Plant Pat. No. 8,281). A large group of these first generation seedlings, growing on their own root system, were planted and maintained under close observation. The present variety, exhibited outstanding fruit characteristics and was selected in 1994 for asexual propagation and commercialization.

ASEXUAL REPRODUCTION OF THE VARIETY

Asexual reproduction of the present variety of nectarine tree was by budding to 'Nemaguard' Rootstock (non-patented), the standard rootstock for nectarines in California, as performed by us in our experimental orchard located near Modesto, Calif., and shows that reproductions run true to the original tree and all characteristics of the tree and its fruit are established and transmitted through succeeding asexual propagation.

SUMMARY OF THE NEW VARIETY

The present variety of nectarine tree is of large size, vigorous and upright in growth and a regular and productive bearer of large size, early maturing, yellow flesh, sweet, sub-acid, fruit with very good flavor and eating quality. The fruit is further characterized by having an attractive high degree of red skin color, firm flesh with good handling and storage quality, relatively uniform in size throughout the tree and holds firm on the tree for 7 to 8 days after maturity. In comparison to the nectarine tree 'Honey Kist' (U.S. Plant Pat. No. 9,333), one of the paternal parents, the new variety has a lower winter chilling requirement of approximately 350 hours and the fruit is approximately 8 days earlier in maturity, and in comparison to the other paternal parent 'Royal Glo' Nectarine (U.S. Plant Pat. No. 8,281), which has fruit with the normal acidic flesh, the flesh of the present variety is mild, sweet, sub-acid and is approximately 1 week later in maturity.

PHOTOGRAPH OF THE VARIETY

The accompanying color photographic illustration shows typical specimens of the foliage and fruit of the present new nectarine variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as true as is reasonably possible in color representation of this type.

DESCRIPTION OF THE VARIETY

The following is a detailed botanical description of the new variety of nectarine tree, its flowers, foliage and fruit, as based on observations of 6 year old specimens budded to 'Nemaguard' Rootstock (non-patented) and grown near Modesto, Calif., with color terminology (except those in common terms) in accordance with Reinhold Color Atlas by A. Kornerup and J. H. Wanscher.

Tree:

*Size.*—Large, normal for nectarine trees. Usually pruned to 10 to 12 feet in height and width for economical harvesting of fruit.

*Vigor.*—Vigorous. Growth of 6 to 7 feet in height and 5 to 6 feet in width the first growing season. Varies with type and depth of soil, fertility and cultural practices.

*Growth.*—Upright. Usually pruned to vase shape to increase sunlight to center of tree to enhance fruit color, increase Brix and keep fruit bearing wood healthy.

*Branching habit.*—Upright. Crotch angle approximately 30 to 35 degrees. Heavy crop load increases crotch angle and width of the tree.

*Productivity.*—Productive. Usually sets 1½ to several times amount of fruit desired. Thinning and spacing of fruit necessary.

*Bearer.*—Regular. Tree has produced heavy crops 5 consecutive years. No alternate bearing observed.

*Fertility.*—Self-fertile.

*Density.*—Medium dense. When tree starts producing, weight of fruit helps spread the width of tree along with pruning out branches with narrow crotch angles.

*Hardiness.*—Tree grown in USDA Hardiness Zone 9. Winter chilling requirement is approximately 400 to 450 hours at or below 45° F. Hardy in all stone fruit growing areas of California.

Trunk:

*Size.*—Large. Average circumference 21 inches measured 13 inches above ground on 6 year old tree.

*Stocky.*—Medium.

*Surface.*—Medium shaggy, increases with age of tree.

*Color.*—Grayish brown to beaver brown (5-D-3) to (5-F-4).

Branches:

*Size.*—Medium. Average circumference 7½ inches measured 36 inches above ground.

*Surface.*—Smooth on new growth, medium rough on old growth, roughness increases with age of growth.

*Lenticels.*—Average number 23 on 4 square inch area. Size—average length ⅛ inch. Average width 1/16 inch. Color—apricot yellow to golden yellow (5-B-6) to (5-B-7).

*Color.*—New growth varies from spring green to golden brown (30-C-8) to (5-D-7). Older, mature growth varies from honey yellow to hair brown (5-D-6) to (5-E-4). Color darkens with age of tree.

Leaves:

*Color.*—Upper surface deep green to dark green (29-E-6) to (29-F-6). Lower surface pea green to light green (29-D-5) to (29-D-8).

*Size.*—Medium, normal for most nectarine varieties. Average length 4 9/16 inches. Average width 1⅜ inches.

*Form.*—Lanceolate.

*Apex.*—Acuminate.

*Base.*—Cuneate.

*Margin.*—Serrate.

*Thickness.*—Medium, normal for most nectarine varieties.

*Surface.*—Upper surface relatively smooth, slightly indented over midrib and pinnate venation, glabrous. Lower surface relatively smooth, small ridges created by midrib and pinnate venation, glabrous.

*Petiole.*—Average length 31/64 inch. Average width 1/16 inch. Color grayish yellow to olive yellow (2-C-6) to (2-C-8).

*Glands* —Reniform. Number varies from 1 to 3, average number 2. Size—medium length, 1/32 inch. Location — upper portion of petiole and base of leaf blade. Color olive green to grayish green (1-D-4) to (1-D-5). Becomes darker from dust and impurities collected on sticky surface.

Flower buds:

*Size.*—Large. Average length 47/64 inches. Average diameter 31/64 inch, measured 4 days before bloom.

*Hardiness.*—Hardy with respect to all stone fruit growing areas of California.

*Form.*—Plump, conical. Becoming elongated with maturity.

*Pedicel.*—Average length 5/64 inch. Average width 1/16 inch. Color—grayish green (1-D-7).

*Pubescence.*—Smooth except for pubescence on outer surface of sepals.

*Color.*—Pastel pink to rose pink (11-A-4) to (11-A-6).

Flowers:

*Size.*—Large, showy. Average height 23/32 inch. Average diameter 1 31/64 inches.

*Petals.*—Number—5, alternately positioned to sepals. Size—large. Average length 39/64 inches. Average width 37/64 inch, Shape—orbicular, narrower at point of attachment. Outer edges vary from smooth to slightly scalloped. Surface slightly cupped inwardly to form bowl around anthers and pistil. Color—pastel pink to rose pink (11-A-4) to (11-A-5).

*Sepals.*—Shape—elongated. Number — five, alternately arranged to petals. Average length 11/64 inch. Average width 9/64 inch. Color—Upper surface yellowish green (28-C-7), glabrous. Lower surface—grayish ruby (12-C-6), pubescent. Color fades with age of flowers.

*Stamens.*—Average number per flower 29. Average length 15/32 inch. Filament color white (1-A-1), turning pale pink with age of bloom. Anther color red to grayish ruby (12-C-6) to (12-C-7).

*Pollen.*—Present, self-fertile. Color—pale yellow to yellow (4-A-3) to (4-A-4).

*Pistil.*—Usually one. Average length 17/32 inch, stigma approximately 3/32 inch below anthers. Color pale yellow (3-A-3).

*Fragrance.*—Very slight.

*Blooming period.*—Date of First Bloom Feb. 22, 2000. Date of Petal Fall Mar. 2, 2000. Varies slightly with climatic conditions.

*Color.*—Pink to light pink (11-A-3) to (11-A-5). Color fades with age of flower. Varies with climatic conditions.

*Pedicel.*—Average length 7/64 inch. Average width 3/32 inch. Color grayish green (28-C-6).

Fruit:

*Maturity when described.*—Firm ripe.

*Date of first picking.*—Jun. 5, 2000.

*Date of last picking.*—Jun. 13, 2000. Varies slightly with climatic conditions.

*Size.*—Average diameter axially 2⅜ to 2½ inches. Average transversely in suture plane 2½ to 2¾ inches. Average weight 172 grams. Average weight varies with fertility of the soil, amount of fruit thinning and climatic conditions.

*Form.*—Nearly globose, slightly elongated.

*Suture.*—Shallow, extend from base to apex.

*Ventral surface.*—Nearly smooth, only slightly lipped near apex.

*Apex.*—Slightly retuse, varies from slightly retuse to very slight point.

*Base.*—Retuse.

*Cavity.*—Rounded to slightly elongated in suture plane. Average depth ¼ inch. Average breadth ½ inch.

Stem:

*Size.*—Average length ⅜ inch. Average diameter ⅛ inch, enlarged at point of fruit attachment.

*Color.*—Yellowish green (30-C-5).

Flesh:

*Ripens.*—Evenly.

*Texture.*—Firm, meaty.

*Fibers.*—Few, small, tender.

*Firmness.*—Firm, similar to fruit of 'Honey Kist' Nectarine (U.S. Plant Pat. No. 9,333).

*Aroma.*—Slight.

*Amydgalin.*—Undetected.

*Eating quality.*—Very good.

*Flavor.*—Very good, sweet, mild, sub-acid.

*Juice.*—Moderate, enhances flavor.

*Brix.*—Average 13.3°. Varies slightly with amount of fruit per tree and climatic conditions.

*Color.*—Maize yellow to sunflower yellow (4-A-6) to (4-A-7). Pit cavity grayish yellow to amber yellow (4-B-4) to (4-B-7).

Skin:

*Thickness.*—Medium, tenacious to the flesh.

*Texture.*—Medium, similar to 'Honey Kist' Nectarine (U.S. Plant Pat. No. 9,333), no problem with tearing or scarring during picking or packing trials.

*Tendency to crack.*—None.

*Pubescence.*—Wanting.

*Color.*—Yellow to golden yellow ground color (4-A-4) to (4-A-5). Overspread with red to Turkish red (10-C-7) to (10-C-8). Small, randomly spaced areas of ground color showing in some areas giving a speckled pattern.

*Tenacity.*—Tenacious to flesh.

*Astringency.*—None.

Stone:

*Type.*—Clingstone.

*Size.*—Large. Average length 1 19/64 inches. Average width 1 1/16 inches. Average thickness 53/64 inch.

*Form.*—Obovoid.

*Base.*—Varies from rounded to flat.

*Apex.*—Varies from very slight point to rounded. Average length—very short, 1/16 inch on some stones.

*Surface.*—Irregularly furrowed toward apex, pitted toward base, pits vary from round to elongated. One long furrow on each side of suture extending from base to apex. Ridges relatively wide and rough.

*Sides.*—Usually unequal with one side extending further from center of suture plane.

*Tendency to split.*—Very slight.

*Color.*—Yellowish brown to light brown (5-C-6) to (5-C-7) when dry.

Kernel:

*Average length.*—21/32 inch.

*Average width.*—15/32 inch.

*Seed coat color.*—Tan to grayish orange (5-B-4) to (5-B-5) when dry.

*Taste.*—Bitter.

*Amydgalin.*—Abundant.

Use: Dessert. Market—local and long distance.

Keeping quality: Good, held firm in cold storage (38° to 42°) for 2 weeks without internal breakdown of flesh.

Shipping quality: Good, fruit showed minimal skin scarring or bruising of flesh during packing and shipping trials.

Disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of nectarine tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of nectarine tree, substantially as illustrated and described, which is of large size, upright growth and a productive and regular bearer of large, yellow flesh, clingstone fruit with very good flavor and eating quality; the fruit is further characterized by having firm flesh with a sweet, sub-acid flavor, having good storage and shipping quality and in comparison to the 'Honey Kist' Nectarine (U.S. Plant Pat. No. 9,333), the new variety has a lower winter chilling requirement of approximately 350 hours and produces fruit that is approximately 8 days earlier in maturity.

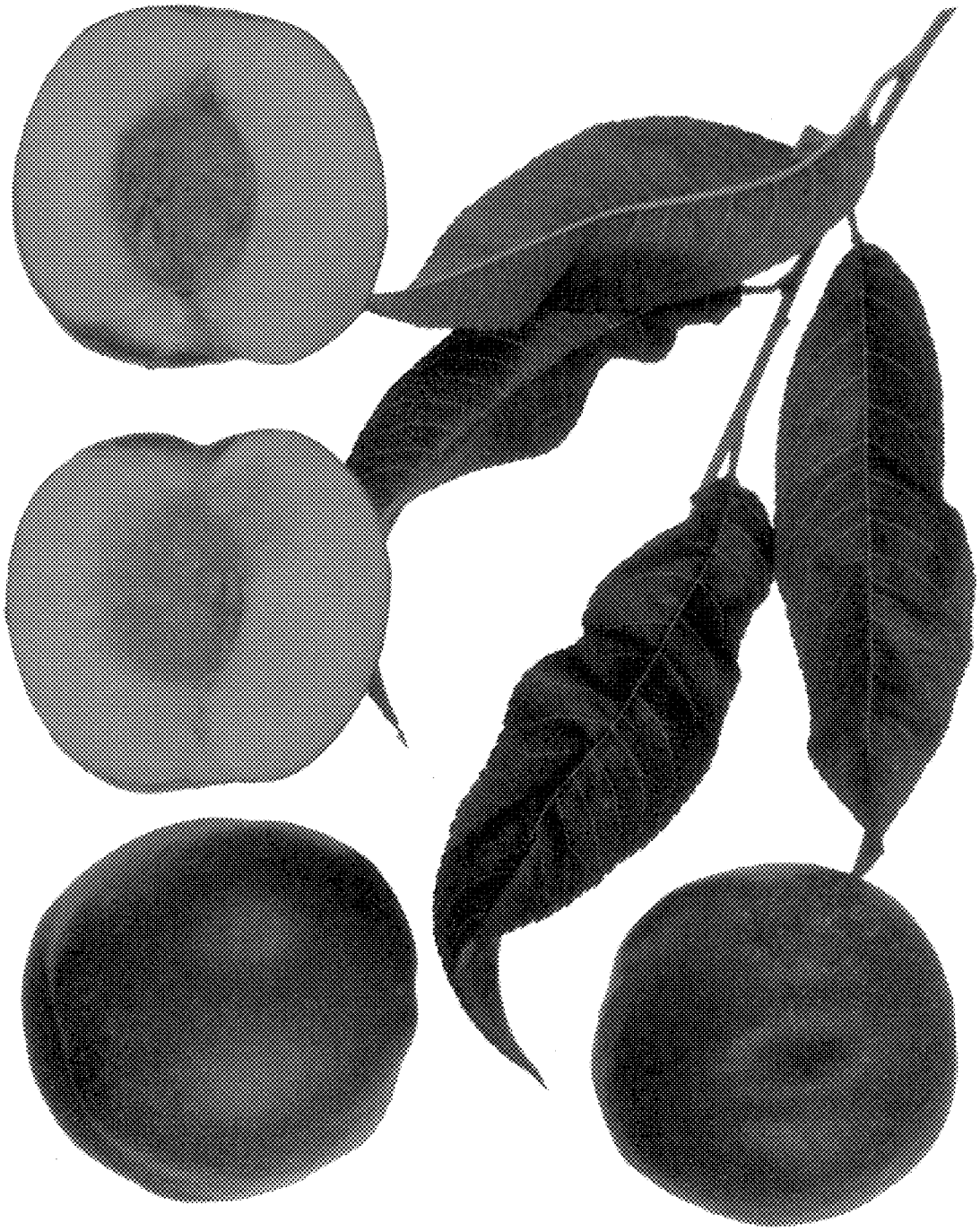

* * * * *